(12) United States Patent
Wolber

(10) Patent No.: US 7,488,575 B2
(45) Date of Patent: Feb. 10, 2009

(54) MULTIDENTATE ARRAYS

(75) Inventor: Paul K. Wolber, Los Altos, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 1248 days.

(21) Appl. No.: 10/271,074

(22) Filed: Oct. 15, 2002

(65) Prior Publication Data

US 2003/0129627 A1 Jul. 10, 2003

Related U.S. Application Data

(62) Division of application No. 09/346,655, filed on Jul. 1, 1999, now Pat. No. 6,465,183.

(51) Int. Cl.
*C12Q 1/68* (2006.01)
(52) U.S. Cl. .......................................................... 435/6
(58) Field of Classification Search ........................ None
See application file for complete search history.

(56) References Cited

U.S. PATENT DOCUMENTS

| | | | |
|---|---|---|---|
| 4,731,325 A | 3/1988 | Pavla et al. | |
| 4,868,105 A | 9/1989 | Urdea et al. | |
| 5,585,481 A | 12/1996 | Arnold, Jr. et al. | |
| 5,604,097 A | 2/1997 | Brenner | |
| 5,614,388 A | 3/1997 | Picone et al. | |
| 5,635,400 A | 6/1997 | Brenner | |
| 5,654,413 A | 8/1997 | Brenner | |
| 5,723,320 A | 3/1998 | Dehlinger | |
| 5,763,175 A | 6/1998 | Brenner | |
| 5,846,719 A | 12/1998 | Brenner et al. | |
| 5,863,722 A | 1/1999 | Brenner | |
| 6,306,643 B1 | 10/2001 | Gentalen et al. | |

FOREIGN PATENT DOCUMENTS

WO    WO 00/11223    3/2000

OTHER PUBLICATIONS

Gentalen, E. and Chee, M., "A Novel Method for Determining Linkage Between DNA Sequences: Hybridization to Paired Probe Arrays", Nucleic Acids Research, 1999, vol. 27, No. 6, pp. 1485-1491.

*Primary Examiner*—Kenneth R. Horlick
*Assistant Examiner*—David C Thomas

(57) ABSTRACT

A method of evaluating for the presence of a target polynucleotide in a sample, using an addressable array of multiple polynucleotide probes linked to a substrate. The sample is exposed to the array and a set of polynucleotide target probes, such that target polynucleotide which may be present will bind to a predetermined feature of the array through multiple target probes of the set by forming at respective target regions on a target molecule, simultaneous hybrids with anti-target regions of the multiple target probes. A binding pattern on the array is observed and the presence of the target polynucleotide evaluated based on the observed binding pattern. Kits using such arrays, and methods for selecting target probes are further provided.

13 Claims, 4 Drawing Sheets

SEQUENCE LISTING

<160> NUMBER OF SEQ ID NOS: 33

<210> SEQ ID NO 1
<211> LENGTH: 25
<212> TYPE: DNA
<213> ORGANISM: Arabidopsis thaliana

<400> SEQUENCE: 1
gtaccagttt ccactaccat cccgg                                         25

<210> SEQ ID NO 2
<211> LENGTH: 25
<212> TYPE: DNA
<213> ORGANISM: Arabidopsis thaliana

<400> SEQUENCE: 2
gaggattcac cagctgtcac gtcca                                         25

<210> SEQ ID NO 3
<211> LENGTH: 25
<212> TYPE: DNA
<213> ORGANISM: Arabidopsis thaliana

<400> SEQUENCE: 3
agaggttacg gatcgtggat tgttt                                         25

<210> SEQ ID NO 4

```
<211> LENGTH: 25
<212> TYPE: DNA
<213> ORGANISM: Arabidopsis thaliana

<400> SEQUENCE: 4
aggagaacaa gattactctg ctaga                                    25

<210> SEQ ID NO 5
<211> LENGTH: 25
<212> TYPE: DNA
<213> ORGANISM: Arabidopsis thaliana

<400> SEQUENCE: 5
tgaggagaac aagcctagtg tcatc                                    25

<210> SEQ ID NO 6
<211> LENGTH: 25
<212> TYPE: DNA
<213> ORGANISM: Arabidopsis thaliana

<400> SEQUENCE: 6
agagtctgat gattaagcaa aatgg                                    25

<210> SEQ ID NO 7
<211> LENGTH: 25
<212> TYPE: DNA
<213> ORGANISM: Arabidopsis thaliana

<400> SEQUENCE: 7
tggttatgtc tattgctcag cgtta                                    25

<210> SEQ ID NO 8
<211> LENGTH: 25
<212> TYPE: DNA
<213> ORGANISM: Arabidopsis thaliana

<400> SEQUENCE: 8
agggtggtct tatcggactt ttgcg                                    25

<210> SEQ ID NO 9
<211> LENGTH: 25
<212> TYPE: DNA
<213> ORGANISM: Arabidopsis thaliana

<400> SEQUENCE: 9
gtcttatcgg acttttgcgg ggaat                                    25

<210> SEQ ID NO 10
<211> LENGTH: 25
<212> TYPE: DNA
<213> ORGANISM: Arabidopsis thaliana

<400> SEQUENCE: 10
ggctatgagt aatgtgcgtt tggtt                                    25

<210> SEQ ID NO 11
<211> LENGTH: 25
<212> TYPE: DNA
<213> ORGANISM: Arabidopsis thaliana

<400> SEQUENCE: 11
gtgcttagtc atgtggaagt tgtgc                                    25
```

```
<210> SEQ ID NO 12
<211> LENGTH: 25
<212> TYPE: DNA
<213> ORGANISM: Arabidopsis thaliana

<400> SEQUENCE: 12
ggtcttcgtc ttgatgatca taagt                                  25

<210> SEQ ID NO 13
<211> LENGTH: 25
<212> TYPE: DNA
<213> ORGANISM: Arabidopsis thaliana

<400> SEQUENCE: 13
ggattcgaca gggtgtctca agagc                                  25

<210> SEQ ID NO 14
<211> LENGTH: 25
<212> TYPE: DNA
<213> ORGANISM: Arabidopsis thaliana

<400> SEQUENCE: 14
tacattgcgg atactcgttt ggaga                                  25

<210> SEQ ID NO 15
<211> LENGTH: 25
<212> TYPE: DNA
<213> ORGANISM: Arabidopsis thaliana

<400> SEQUENCE: 15
cacttggcgg atccatggca caaca                                  25

<210> SEQ ID NO 16
<211> LENGTH: 25
<212> TYPE: DNA
<213> ORGANISM: Arabidopsis thaliana

<400> SEQUENCE: 16
ggattctgtg tgcaacagtc ggctt                                  25

<210> SEQ ID NO 17
<211> LENGTH: 25
<212> TYPE: DNA
<213> ORGANISM: Arabidopsis thaliana

<400> SEQUENCE: 17
gcgctgttgg cgtttgtagg attct                                  25

<210> SEQ ID NO 18
<211> LENGTH: 25
<212> TYPE: DNA
<213> ORGANISM: Arabidopsis thaliana

<400> SEQUENCE: 18
ggagaacttg gcaactcact tggcg                                  25

<210> SEQ ID NO 19
<211> LENGTH: 25
<212> TYPE: DNA
<213> ORGANISM: Arabidopsis thaliana

<400> SEQUENCE: 19
gtgtacctta tgagctttat gtgta                                  25
```

```
<210> SEQ ID NO 20
<211> LENGTH: 25
<212> TYPE: DNA
<213> ORGANISM: Arabidopsis thaliana

<400> SEQUENCE: 20
aacattggcg atattgttat ccctt                                   25

<210> SEQ ID NO 21
<211> LENGTH: 25
<212> TYPE: DNA
<213> ORGANISM: Arabidopsis thaliana

<400> SEQUENCE: 21
gctcactgga tgcctggcga gccac                                   25

<210> SEQ ID NO 22
<211> LENGTH: 25
<212> TYPE: DNA
<213> ORGANISM: Arabidopsis thaliana

<400> SEQUENCE: 22
cattgcattt gttgagcacc agaga                                   25

<210> SEQ ID NO 23
<211> LENGTH: 25
<212> TYPE: DNA
<213> ORGANISM: Arabidopsis thaliana

<400> SEQUENCE: 23
ggtttgaccc acttggactt ggaga                                   25

<210> SEQ ID NO 24
<211> LENGTH: 25
<212> TYPE: DNA
<213> ORGANISM: Arabidopsis thaliana

<400> SEQUENCE: 24
gttcctggga ttttggtacc agaag                                   25

<210> SEQ ID NO 25
<211> LENGTH: 25
<212> TYPE: DNA
<213> ORGANISM: Escherichia coli

<400> SEQUENCE: 25
gcaggttgct cgtctgcttg atcct                                   25

<210> SEQ ID NO 26
<211> LENGTH: 25
<212> TYPE: DNA
<213> ORGANISM: Escherichia coli

<400> SEQUENCE: 26
ctcactatgc aggttgctcg tctgc                                   25

<210> SEQ ID NO 27
<211> LENGTH: 25
<212> TYPE: DNA
<213> ORGANISM: Escherichia coli

<400> SEQUENCE: 27
ggttatttcc ggtggcagca cgctc                                   25
```

```
<210> SEQ ID NO 28
<211> LENGTH: 25
<212> TYPE: DNA
<213> ORGANISM: Escherichia coli

<400> SEQUENCE: 28
tgcttgatcc tcaccccaaa acatt                                  25

<210> SEQ ID NO 29
<211> LENGTH: 25
<212> TYPE: DNA
<213> ORGANISM: Escherichia coli

<400> SEQUENCE: 29
ctcacttcgg gacgggttat ttccg                                  25

<210> SEQ ID NO 30
<211> LENGTH: 25
<212> TYPE: DNA
<213> ORGANISM: Escherichia coli

<400> SEQUENCE: 30
gtggtcccgt gagcaggtaa aagag                                  25

<210> SEQ ID NO 31
<211> LENGTH: 25
<212> TYPE: DNA
<213> ORGANISM: Escherichia coli

<400> SEQUENCE: 31
atgcgtgttc gcggctgggt gggat                                  25

<210> SEQ ID NO 32
<211> LENGTH: 25
<212> TYPE: DNA
<213> ORGANISM: Escherichia coli

<400> SEQUENCE: 32
ggcggtacgt tgcaggggat cggtg                                  25

<210> SEQ ID NO 33
<211> LENGTH: 25
<212> TYPE: DNA
<213> ORGANISM: Escherichia coli

<400> SEQUENCE: 33
ggattgccgt tatatttgcc caacg                                  25
```

MULTIDENTATE ARRAYS

This is a Divisional application Ser. No. 09/346,655, filed on Jul. 01, 1999 now U.S. Pat. No. 6,465,183, the entire disclosure of which is incorporated herein by reference.

FIELD OF THE INVENTION

This invention relates to arrays, particularly biopolymer arrays such polynucleotide arrays, which are useful in diagnostic, screening, gene expression analysis, and other applications.

BACKGROUND OF THE INVENTION

Arrays of biopolymers, such as arrays of peptides or polynucleotides (such as DNA or RNA), are known and are used, for example, as diagnostic or screening tools. Such arrays include regions (sometimes referenced as features or spots) of usually different sequence biopolymers arranged in a predetermined configuration on a substrate. The arrays, when exposed to a sample, will exhibit a pattern of binding which is indicative of the presence and/or concentration of one or more components of the sample, such as an antigen in the case of a peptide array or a polynucleotide of particular sequence in the case of a polynucleotide array. The binding pattern can be detected, for example, by labeling all potential targets (for example, DNA) in the sample with a suitable label (such as a fluorescent compound), and accurately observing the fluorescence pattern on the array.

In one application, arrays of oligonucleotide probes provide useful tools for simultaneous evaluation of the levels of expression of large sets of genes ("expression profiling"). The probe arrays used in expression profiling can be produced in two ways: (i) oligonucleotide probes can be synthesized in situ on the array surface, using location-addressable adaptations of phosphoramidite chemistry (for example, photo-deprotection, or printing of phosphoramidites using an inkjet type printer); (ii)whole oligonucleotide probes synthesized either by phosphoramidite chemistry or enzymatic methods (for example, PCR) can be deposited on a surface designed to form either a strong non-covalent attachment to DNA (for example, poly-L-lysine) or a covalent attachment to a chemically unique group added to the oligonucleotide during synthesis (for example, a modified base containing a primary aliphatic amine). Noncovalent attachment may be subsequently turned into covalent attachment by methods such as UV photo-cross linking. Chemical synthesis is used to produce probes shorter than 50 nucleotides, while enzymatic methods are used to produce longer probes (100-1000 nucleotides).

Synthetic nucleotide probes (either synthesized in situ or deposited whole) can potentially discriminate between closely related mRNA's, because they can be designed to probe the most different portions of the target sequences, and because the effects of these differences are proportionately greater for shorter probes. This ability is important, because many genes in higher organisms are members of families of related genes. However, shorter probes suffer from the difficulty that they do not associate with their targets as strongly as longer probes (that is, they have a lower binding constant or binding affinity). This weaker association makes it very difficult to produce oligonucleotide probes that can unequivocally detect concentrations lower than 0.1 pM for the best cases, and typical detection limits are in the range of 1 pM-10 pM. This results in a sensitivity gap. For example, if all of the mRNA in a sample of $10^6$ cells (a typical size for sampling a precious specimen, such as a biopsy sample) is converted into labeled cDNA, and the resulting material is resuspended in a volume of 100 µl, then the final concentration of the cDNA derived from a message present at 1 copy per cell is $$\frac{(10^6 \text{ cells})\left(\frac{1 \text{copy}}{\text{cell}}\right)}{\left(6.02 \times 10^{23} \frac{\text{copies}}{\text{mole}}\right)(10^{-4} \text{ liters})} = 1.66 \times 10^{-14} \text{ M} = 0.017 \text{ pM}$$

This is a factor of 5 lower than the lowest limit of detection achieved with current oligonucleotide probe—polynucleotide target combinations, and a factor of 50-500 below more typical detection limits.

The sensitivity gap can be closed by employing a target amplification scheme, such as linear amplification by RNA transcription or asymmetric PCR. However, this adds both complication and cost to the assay. In addition, losses of mRNA during sample preparation, amplification, inhibition by sample-derived impurities and problems with probe specificity (which necessitate more stringent conditions and lower signal levels) can together use up most or all of the sensitivity margin provided by target amplification. Finally, lowering the number of cells required per sample would greatly improve the applicability of arrays, since it would then be possible to perform entire array analyses on samples provided by microsampling methods, such as needle biopsy and laser-assisted micro-dissection.

Arrays which utilize longer probes can exhibit binding constants high enough to yield detection limits in the $10^{-15}$ M range. However, this improved performance comes at the costs of lost specificity within gene families and loss of the ability of design probes to hybridize to the most unique target subsequences.

Solutions to the sensitivity gap from using synthetic oligonucleotide probes, include target amplification, signal amplification, the use of high sensitivity labels and the use of modified probe nucleotide chemistries. Target amplification, described in the previous section, is a well established method for overcoming an intrinsic binding constant that is too low. It solves the problem directly, by increasing the amount of target by a well-controlled factor that is relatively independent of the target sequence. The disadvantages of target amplification are the complication and cost added to sample preparation. Another solution is signal amplification, which is achieved by multiplying the number of detectable labels attached to a given target molecule that binds to an array feature. Many sample labeling schemes incorporate a basic form of signal amplification by the simple expedient of attaching the label (for example, a fluorophore) to one or more of the nucleotide triphosphates used by the transcription-based system that produces labeled target oligonucleotide. More elaborate schemes, such as binding of labeled biotin-streptavidin complexes and the formation of sandwiches between surface-bound probes, unlabeled targets and highly labeled second probes (for example, branched DNA probes) have also been employed. These methods, like target amplification, are relatively costly and complicated and further rely on the binding of a very small number of molecules. This can result in an added source of noise derived from the probabilistic binding of small numbers of target molecules. High sensitivity labels (for example, radioisotopes, chemiluminescent labels) are a special case of signal amplification. The main advantage of such methods is that they generate signal against a very low intrinsic background. The disadvantage is that these labels are not as convenient or safe as fluorescent probes. In addition, radioisotopes provide lower spatial resolution than optical probes.

Probes that incorporate modified bases or backbones into polynucleotides may be capable of providing much higher per base binding free energies than conventional DNA probes. The main disadvantages of this approach are the relatively poor state of development of synthetic schemes for producing probes that incorporate nucleotide analogues and the relatively poor state of characterization of the benefits derived from the use of such alternate chemistries. At present most of the performance enhancement available from modified polynucleotide chemistries is theoretical.

U.S. Pat. No. 4,731,325 describes an arrangement using two or three identifying nucleic acid fragments homologous to a nucleic acid to be identified. The patent states that if simultaneous identification of several different nucleic acids is desired, it is necessary to use separate filters to which are attached the required fragments. A paper by Gentalen et al., "A novel method for determining linkage between DNA sequences: hybridization to paired probe arrays" *Nucleic Acids Research*, 1999, Vol. 27, No. 6 1485-1491 describes co-operative hybridization to establish physical linkage between two loci on a DNA strand. These reference, and all other references cited in this application, are incorporated in this application by reference. However, cited references or art are not admitted to be prior art to this application.

It would be desirable then, to provide a means for detecting a target using probes, particularly in the form of an addressable array, which can provide good binding affinity for the target. It would also be desirable that any such means be relatively simple to fabricate. It would further be desirable that a means be provided for aiding in the selection of such probes.

SUMMARY OF THE INVENTION

The present invention then, provides for high affinity of probes to a target by using an array feature in which two or more probes are present which together bind with respective regions of a target at two or more regions (that is, the feature exhibits "multidentate" binding"). Furthermore, the present invention appreciates that in the context of such systems, due to secondary structure of target polynucleotide in particular, finding a good set of target probes is not necessarily a matter of simply selecting probe sequences complementary to target sequences of the target polynucleotide. The invention then, also provides for a means aiding in the selection of probes suitable to provide the foregoing multidentate binding.

In one aspect, the present invention provides a method of evaluating for the presence of a target polynucleotide in a sample, using an addressable array of multiple polynucleotide probes linked to a substrate. The sample is exposed to the array and a set of polynucleotide target probes, such that target polynucleotide which may be present will bind to a predetermined feature of the array through multiple target probes of the set. This occurs by respective target regions on a target molecule, forming simultaneous hybrids with anti-target regions of the target probes. It will be appreciated, of course, that the target probe set is either bound to the substrate either before, during, or after exposure to the substrate. For example, the target probe can be either directly bound to the substrate (for example, by linking to the substrate before the sample is exposed to the array), or indirectly bound to the substrate (such as through a capture probe). Thus, individual target molecules will be bound to the array at multiple locations along the molecule (sometimes referenced herein as "multidentate binding").

Optionally, a binding pattern on the array may then be observed and the presence of the target polynucleotide evaluated based on the observed binding pattern. However, this can be done either within a short time following the foregoing steps, or potentially at some indefinite later time.

The method of the invention also allows for the presence of multiple different target polynucleotides to be evaluated. In this mode, the sample is exposed to multiple different sets of target probes such that each of the different polynucleotide molecules which may be present will bind to a corresponding predetermined features of the array through multiple target probes of a corresponding set by forming at respective target regions, simultaneous hybrids with the multiple probes of the corresponding set. Thus, each particular type of target molecule will be bound to the corresponding feature of the array at multiple locations along the molecule. Note however, throughout this invention a given target polynucleotide can in fact be a class of polynucleotides in which no discrimination is required between individual members of the class. In such a case, a member of the class may have target regions which are the same or similar in sequence to other members of the class.

In an aspect of the invention where the target probes are to be indirectly bound to the substrate, the target probes also include anti-capture regions. Also, the predetermined feature of the array includes a set of capture probes linked to the substrate which have capture regions which will hybridize with the anti-capture regions. In this manner, multiple molecules of a given type of target polynucleotide which may be present will each indirectly bind to the predetermined feature through the corresponding set of target probes, by the anti-target regions of target probes forming the simultaneous hybrids with the respective target regions and by the anti-capture regions hybridizing with the capture regions of the capture probes. Alternatively, the capture probes may not be linked to the substrate, in which case the predetermined region of the substrate should be provided with a further probe to bind to some region of the capture probe (that is, the target would become bound to the substrate at least through a set of target probes, a set of capture probes, and some other probes at the predetermined feature on the array).

Note that in the invention, the target regions of any one target polynucleotide (that is, any one type of target polynucleotide) could be of the same sequence (in which case, the members of the set of target probes can be the same, that is the "set" corresponding to that target polynucleotide has only one member in the form of one type of target probe) or of different sequence (in which case the anti-target regions of the multiple target probes of the set may also be of different sequence to hybridize with the different sequenced target regions—thus the "set" has more than one member in the form of multiple types of target probes). For example, target regions of a given polynucleotide may differ from one another by at least two (or three, or four) nucleotides, while the anti-target regions of the corresponding probe set also differ from one another by at least two (or three, or four) nucleotides. However, it will be appreciated that when there is more than one target polynucleotide (that is more than one type of target polynucleotide), target regions of one target polynucleotide should be of different sequence from those of another target polynucleotide so that one does not bind to the array feature intended for the other. In the case of indirect binding of target to the array using capture probes, anti-target regions within a given target probe set may also be the same or different. Also, the anti-capture regions within a given probe set may be the same or different. It will also be appreciated in the present method that any target nucleotide may be determined to be present (positive test) or not present (negative test) based on the observed binding pattern.

The present invention further provides an apparatus which can be used in methods of the present invention to evaluate for the presence of a target polynucleotide in a sample. Such an apparatus includes an addressable array of multiple polynucleotide probes linked to the substrate. The apparatus further includes a set of polynucleotide target probes which may or may not be linked to the substrate as part of the array. By this arrangement, target polynucleotide which may be present in a sample exposed to the array will bind to a predetermined feature of the array through multiple target probes of the set by forming at respective target regions on a target molecule, simultaneous hybrids with anti-target regions of the multiple target probes. Again, the target regions may be of the same or different sequence. In the case where the target regions are of different sequence, the set of target probes has at least two target probes with different sequence anti-target regions. For ease of reference, an apparatus for evaluating the presence of a target polynucleotide will sometimes be referred to in this application as a "kit" to distinguish from the apparatus of the present invention for evaluating target probes. However, it will be appreciated that such a "kit" may be simply an array (and hence, an "array of the present invention" is also referenced).

In one aspect, where the presence of multiple different target polynucleotides are to be evaluated by the apparatus, the apparatus includes multiple different sets of target probes. In this manner the different polynucleotide molecules which may be present in the sample will bind to respective different predetermined features of the array through multiple target probes of respective sets, by forming at respective target regions, simultaneous hybrids with the multiple probes of the respective sets.

In a particular aspect, the anti-target regions of the multiple target probes of all the sets may be of different sequence. This is distinguished from the case where anti-target regions of target probes within a given set may be the same, where the target regions of the target corresponding to that set are of the same sequence. In this case the designer of target probes may wish to specifically select candidate probes which will bind to such repeated regions in order to promote multidentate binding. Also, the apparatus may include target probes linked to the predetermined array feature (for direct target binding) or may additionally include target probes not linked to the substrate (for indirect target binding), both as described above. Similarly, the apparatus may include an array, and probe sets suitable for carrying out any of the methods of the present invention.

The present invention further provides a method of evaluating polynucleotide target probes on their ability to form simultaneous hybrids with respective regions of a same target polynucleotide molecule. The method includes selecting candidate probes which can potentially hybridize with selected respective candidate target regions of the target polynucleotide, based on the sequence of the selected candidate target regions. While the candidate probes will typically be exact complements of the selected candidate target regions, they need not necessarily be so. The candidate probes are tested on their ability to actually hybridize individually with respective candidate target regions. At least two of the candidate probes are further selected, which actually hybridized individually with at least a predetermined efficiency with respective candidate target regions. The further selected candidate probes are tested on their ability to form simultaneous hybrids with the respective candidate target regions. Optionally, multiple different relative concentrations of the further selected candidate probes may be tested in the foregoing manner.

In a particular aspect of the evaluation method, the target probes are evaluated on their ability to form the simultaneous hybrids, when the probes are linked to a substrate (such as that of a polynucleotide array). In this case, at least the further selected candidate probes are tested on their ability to form simultaneous hybrids, when linked to the same substrate. Further, the initially selected candidate probes may also be linked to a substrate when being tested on their ability to actually hybridize individually with respective candidate target regions. In either case, the initially or further selected candidate probes may be linked to the same substrate in the form of an addressable array.

In the evaluation method of the present invention, the selected respective candidate target regions may be spaced apart along the target polynucleotide (such as at regular or irregular intervals, or based upon regions which from other analysis are thought to be particularly good target regions). The method may additionally include selecting at least one additional candidate target region based on a hybridization pattern (such as the efficiency of binding) of those candidate probes tested on their ability to actually hybridize individually, and repeating the selecting and testing candidate probes to hybridize individually, for the additional candidate target region. Additional iterations of these steps can optionally be repeated as often as desired.

The present invention further provides a method of fabricating an addressable array of multiple polynucleotide probes linked to a substrate. In this method, target probes are evaluated according to the method above. Further selected candidate probes which actually formed simultaneous hybrids with the respective candidate target regions with at least a predetermined efficiency, are linked to the substrate at a predetermined feature.

The present invention further provides an apparatus comprising a computer for evaluating polynucleotide target probes on their ability to form simultaneous hybrids with respective regions of a same target polynucleotide molecule. In one aspect, the apparatus executes at least the steps of: (a) selecting candidate probes which can potentially hybridize with selected respective candidate target regions of the target polynucleotide, based on the sequence of the selected candidate target regions; (b) receiving results of testing candidate probes on their ability to actually hybridize individually with respective candidate target regions; (c) further selecting at least two of the candidate probes which actually hybridized individually with at least a predetermined efficiency with respective candidate target regions. In another aspect, the executed steps include the foregoing steps (a) and (b) and a step (c) in which at least one additional candidate target region based on the results received in step (b) is selected, and at least step (a) repeated for the additional candidate target region. In a still further aspect, the computer may additionally receive results of testing the further selected candidate probes on their ability to simultaneously hybridize with respective target regions of the target polynucleotide. These results can optionally include the testing of the further selected candidate probes on their ability, at multiple different relative concentrations, to simultaneously hybridize with respective target regions of the target polynucleotide. In a still further particular aspect, these results at multiple different concentrations can be analyzed and a relative concentration of the members of the set of such candidate probes selected, and optionally linked to a substrate at a predetermined feature (typically along with other probes at their respective features) to produce an array of the present invention.

A computer program product is further provided by the present invention, which includes a computer readable storage medium having a computer program stored on the medium for performing, when loaded into a computer, at least the steps of any of the methods or apparatus of the present invention.

It will be appreciated that while in the above description reference is made to polynucleotides, the present invention can be extended to other target moieties and suitable probes, for example, to biopolymers other than polynucleotides, such as peptides (which is used here to include proteins). Thus, a description of a broader aspect of the present invention may be obtained simply by deleting "polynucleotide" in the description of the invention, and replacing "hybridizing" or similar terms with simply "binding", and "hybrids" with "binding partners". In one aspect, "polynucleotide" can be replaced with "biopolymer", or in a particular aspect with "peptide".

The various aspects of the present invention can provide any one or more of a number of useful benefits. For example, a means is provided for detecting a target using probes, particularly in the form of an addressable array, which can provide good binding affinity for the target. Such means is relatively simple to fabricate. A means is further provided for aiding in the selection of such probes.

BRIEF DESCRIPTION OF THE DRAWINGS

Embodiments of the invention will now be described with reference to the drawings in which.

To facilitate understanding, identical reference numerals have been used, where practical, to designate similar elements that are common to the figures.

DETAILED DESCRIPTION OF THE INVENTION

Figure 1:
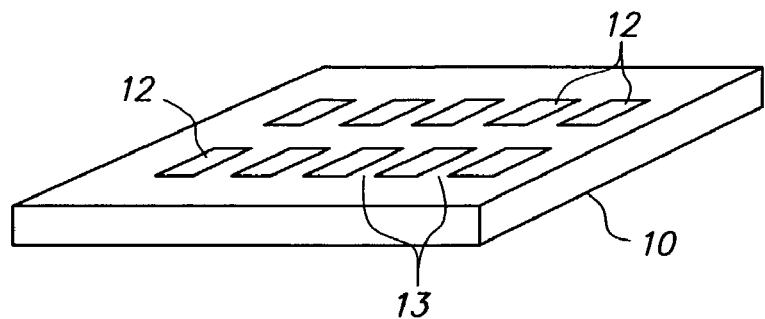
FIG. 1 illustrates a chip carrying multiple arrays, at least one of which is of the present invention, wherein target probes are directly linked to the substrate.

Throughout the present application, unless a contrary intention appears, the terms following terms refer to the indicated characteristics. A "biopolymer" is a polymer of one or more types of repeating units. Biopolymers are found in biological systems and particularly include peptides or polynucleotides, as well as such compounds composed of or containing amino acid or nucleotide analogs or non-nucleotide groups. This includes polynucleotides in which the conventional backbone has been replaced with a non-naturally occurring or synthetic backbone, and nucleic acids in which one or more of the conventional bases has been replaced with a synthetic base capable of participating in Watson-Crick type hydrogen bonding interactions. Polynucleotides include single or multiple stranded configurations, where one or more of the strands may or may not be completely aligned with another. While probes and targets of the present invention will typically be single-stranded, this is not essential. A "nucleotide" refers to a sub-unit of a nucleic acid and has a phosphate group, a 5 carbon sugar and a nitrogen containing base, as well as analogs of such sub-units. Specifically, a "biopolymer" includes DNA (including cDNA), RNA and oligonucleotides, regardless of the source. An "oligonucleotide" generally refers to a nucleotide multimer of about 10 to 100 nucleotides in length, while a "polynucleotide" includes a nucleotide multimer having any number of nucleotides. A "biomonomer" references a single unit, which can be linked with the same or other biomonomers to form a biopolymer (for example, a single amino acid or nucleotide with two linking groups one or both of which may have removable protecting groups). A biomonomer fluid or biopolymer fluid reference a liquid containing either a biomonomer or biopolymer, respectively (typically in solution). An "array", unless a contrary intention appears, includes any one or two dimensional arrangement of addressable regions bearing particular biopolymer moieties (for example, different polynucleotide sequences) associated with that region. An array is "addressable" in that it has multiple regions of different moieties (for example, different sequences) such that a region at a particular predetermined location (an "address") on the array (a "feature" of the array) will detect a particular target or class of targets (although a feature may incidentally detect non-targets of that feature). In the present case, the polynucleotide (or other) target will be in a mobile phase (typically fluid), while probes for the target ("target probes") may or may not be mobile (as described in this application). "Hybridizing" and "binding", with respect to polynucleotides, are used interchangeably. "Binding efficiency" refers to the productivity of a binding reaction, measured as either the absolute or relative yield of binding product formed under a given set of conditions in a given amount of time. "Hybridization efficiency" is a particular sub-class of binding efficiency, and refers to binding efficiency in the case where the binding components are polynucleotides. It will also be appreciated that throughout the present application, that words such as "upper", "lower" are used in a relative sense only. A "set" may have one type of member or multiple different types. "Fluid" is used herein to reference a liquid. By one item being "remote" from another is referenced that they are at least in different buildings, and may be at least one, at least ten, or at least one hundred miles apart. Reference to a singular item, includes the possibility that there are plural of the same items present.

Figure 2:
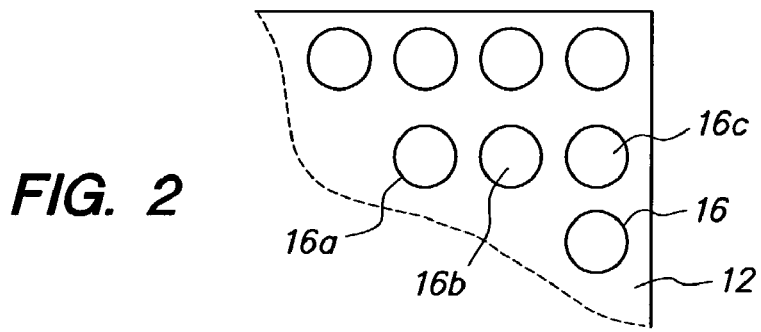
FIG. 2 is an enlarged view of a portion of FIG. 1 showing multiple spots or regions of one array.
Figure 3:
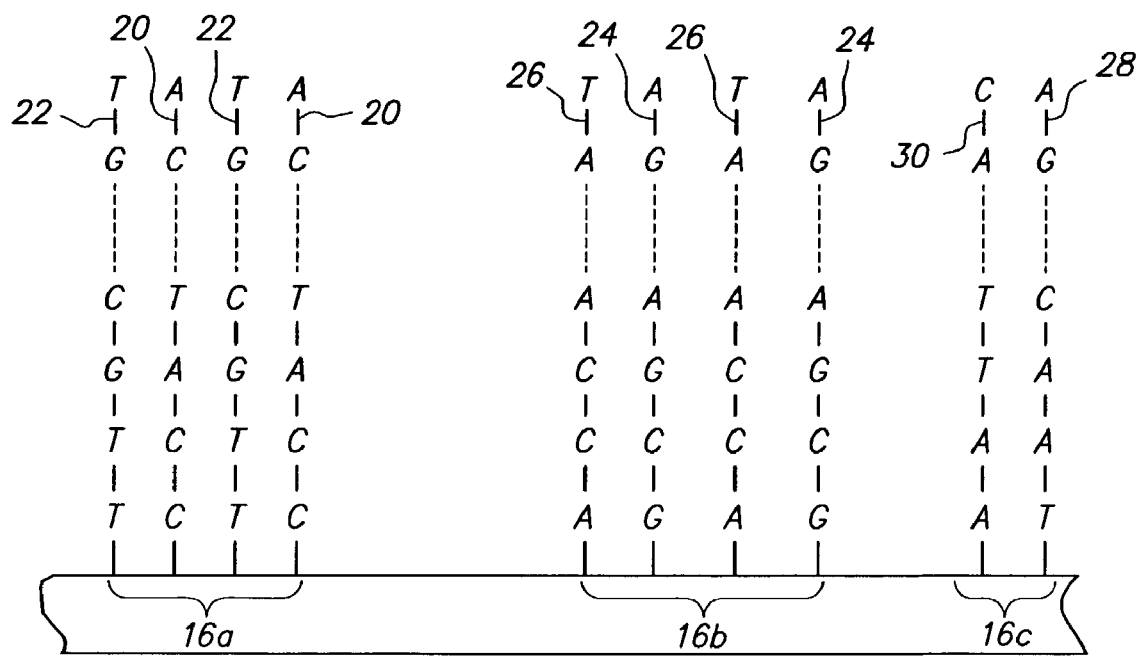
FIG. 3 is an enlarged illustration of a portion of the substrate of FIG. 1.

Referring first to FIGS. 1-3, typically kits and methods of the present invention use a contiguous planar substrate 10 carrying multiple arrays 12 disposed across a first surface 11a of substrate 10 and separated by areas 13. The arrays on substrate 10 can be designed for testing a sample or for evaluating probes on their ability to form hybrids. While ten arrays 12 are shown in FIG. 1 and the different embodiments described below may use substrates with particular numbers of arrays, it will be understood that substrate 10 and the embodiments to be used with it, may use any number of desired arrays 12. Similarly, substrate 10 may be of any shape, and any apparatus used with it adapted accordingly. Depending upon intended use, any or all of arrays 12 may be the same or different from one another and each will contain multiple spots or features 16 of biopolymers in the form of polynucleotides. A typical array may contain from 100 to 100,000 regions. All of the features 16 may be different, or some or all could be the same. Each feature carries a predetermined polynucleotide having a particular sequence, or a predetermined mixture of polynucleotides. It will be appreciated though, that there need not be any space separating arrays 12 from one another, nor features 16 within an array from one another.

FIG. 3 particularly illustrates an addressable array of multiple sets of polynucleotide probes linked to substrate 10 and forming part of the array, wherein features 16 (specifically, each of features 16a, 16b, and 16c) are shown as each carrying sets of polynucleotide target probes. Such an array is useful in kits of the present invention for evaluating for the presence of multiple different polynucleotides, or in testing the ability of multiple different candidate probes of a set to simultaneously hybridize with respective target features of a particular target, as will be described further below. Specifically, feature 16a carries a first set of polynucleotide target probes or candidate target probes, which set has two members of different sequence, namely probes 20, 22. Similarly, feature 16b carries a second set of polynucleotide target or candidate target probes 24, 26, respectively, while feature 16c carries a third set of target or candidate target probes 28, 30, respectively. Thus each feature 16, as illustrated in FIG. 3, can bind to two target features. Typically, the entire sequence of each probe 20, 22, 24, 26, 28, 30 will serve as the anti-target region. It will be appreciated that FIG. 3 is not to scale and that, in particular, each of the features 16 will have many more polynucleotide molecules of each set than illustrated.

The array of FIGS. 1-3 can be used to evaluate for the presence of multiple polynucleotides in a sample by exposing the sample to the array under hybridizing conditions (that is, conditions which allow target sequences to hybridize to corresponding anti-target sequences). Thus, the sample is exposed to multiple different sets of target probes. It will be assumed for this example, that the entire sequences of the target probes in FIGS. 1-3 act as anti-target sequences. Spots 16a, 16b, 16c will allow for the evaluation of the presence of three different polynucleotide targets. In particular, a first target polynucleotide having two different sequence target regions sufficiently complementary (often, but not necessarily, exactly complementary) to respective target probes 20, 22 of the first set, when present will bind to feature 16a through the multiple target probes 20, 22 by forming at respective target regions on a given target molecule, simultaneous hybrids with the a probe 20 and a probe 22. By forming "simultaneous hybrids" throughout this application does not imply any particular order of formation, but only that the hybrids exist at the same time. Thus, the first target is bound to substrate 10 at its two target regions. Similarly, a second target polynucleotide which may be present, will bind to feature 16b through two target regions and complementary respective probes 24, 26. Likewise, a third target polynucleotide which may be present, will bind to feature 16c through two target regions and complementary respective probes 28, 30. Similarly, other features 16 can bind to respective targets although, of course, other features need not bind targets at two regions (but could bind at just one, three, or another number of regions). The resulting binding pattern (which includes the possibility of no binding on the array), can be observed (such as by detection of fluorescence in the case of fluorescently labeled target polynucleotides) and conclusions drawn as to the presence or absence of the different targets in the sample and optionally, of their concentrations (whether relative or absolute).

Figure 4:
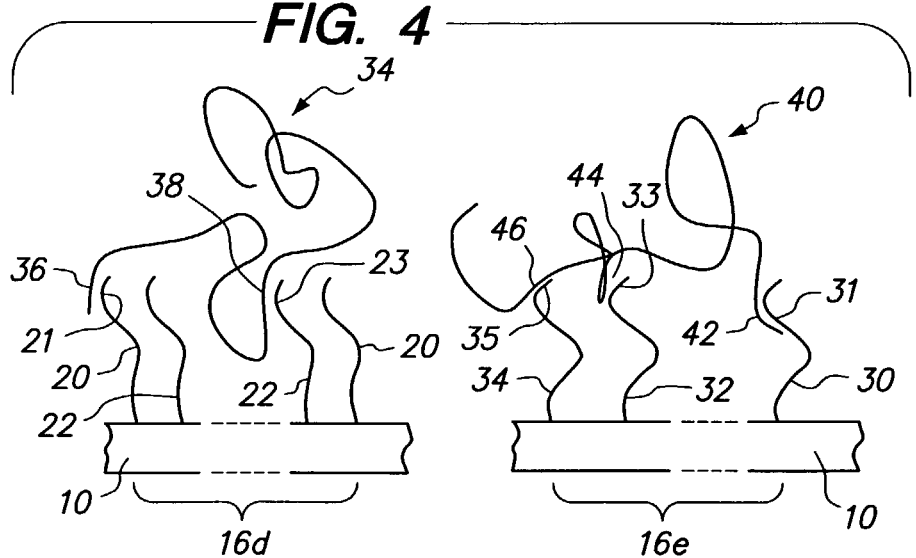
FIG. 4 is an enlarged illustration of a portion of another array and a method of the present invention, wherein target probes are directly linked to the substrate.

If desired, the array particularly illustrated in FIG. 3 can be fabricated so that one or more target probe sets can each form simultaneous hybrids with three or more target regions on a corresponding target probe. This can be accomplished by providing one of the target probe sets at a predetermined feature, with at least three polynucleotide target probes with different sequence anti-target regions. Where the entire length of a target probe is used as the anti-target region, as is typical in FIG. 3, this means that a give array feature will carry at least three different sequence anti-target probes. A portion of an array with a set of three probes having of different anti-target sequence, is illustrated in FIG. 4. In FIG. 4 the illustrated portion of the array has an feature 16d with two a first set of target probes 20, 22 with different sequence anti-target regions 21 and 23, respectively. Note that in this embodiment, only a portion of the illustrated target probes serve as anti-target regions. However, it will be appreciated as mentioned above, that the entire target probe sequence may serve as the anti-target sequence. The array further has an feature 16e with a second set of target probes 30, 32, 34 with respective anti-target regions 31, 33, and 35.

When an array having the features 16d, 16e of FIG. 4 is exposed to a sample to evaluate for the presence of target polynucleotides 34 and 40, target polynucleotide 34 which may be present will bind to feature 16d by forming at respective two target regions 36 and 38, simultaneous hybrids with anti-target regions 21 and 23, respectively. Similarly, target polynucleotide 40 which may be present will bind to feature 16e by forming at three target regions 42, 44, 46, simultaneous hybrids with respective anti-target regions 31, 33 and 35, as illustrated in FIG. 4. Again the resulting binding pattern can be observed and the presence of polynucleotides 34, 40 evaluated based on the observed binding pattern.

Arrays with features such as those illustrated in FIG. 3 or 4 (with mixed probe features), can be produced by mixing two or more pre-synthesized probes (as required by each probe set), then spotting the mixture onto a surface designed to bind the mixture by covalent linkage to a functional group not normally present in oligonucleotides (for example, a primary aliphatic amine or a sulfhydryl group) or by non-covalent absorption and subsequent chemical or photochemical cross-linking. Alternatively, the features can be synthesized in situ on the substrate using phosphoramidite units with two distinct protection chemistries and an ink jet type dispenser. Techniques using different protection chemistries are known. The resulting feature will display a random microscopic mosaic of the probes in the original mixture. A given target molecule will then be capable of binding (by forming simultaneous hybrids) with the multiple, different probes of the corresponding probe set, as described above. Note that each binding targets a different target sequence of the target polynucleotide. If the target polynucleotide is sufficiently flexible, or the target probes are sufficiently numerous, the binding events will take place independently, and the overall binding constant will be the product of the individual binding constants. Thus, such multidentate features are capable of detecting lower concentrations of a target polynucleotide than would a corresponding monodentate feature (that is, a feature which only binds to a target polynucleotide at a single region) carrying only one of the target probes of a multidentate feature.

The features illustrated in FIGS. 3 and 4 have the target probes directly bound to substrate 10. However, as mentioned above, in another aspect of the invention the target probes can be indirectly bound to the substrate. Such a configuration is similar to the directly bound configurations described above except that polynucleotide capture probes are bound to the substrate, and each capture probe of a capture probe set includes both an anti-target region and an anti-capture region which can bind to capture probes in turn bound to the substrate at a corresponding array feature. Thus, the target probes act as intermediate or "bridging probes" between capture probes and target regions. This configuration can be understood with reference to FIG. 5 in particular and is discussed below.

In particular, let X denote a surface bound probe sequence (a capture region) at a predetermined array feature and which is unrelated to any target regions of interest. Let $\overline{X}$ (an anti-capture region on a target probe) denote the sequence exactly complementary to X. Further, let $S_1$, $S_2$, and the like denote different target probe sequences (anti-target regions) of a target probe set, directed against exactly complementary target regions (denoted $\overline{S}_1$, $\overline{S}_2$ and the like) in some target polynucleotide. Let I denote a general intervening sequence in any target probe between an anti-capture region ($\overline{X}$), and the anti-target region ($S_1$, $S_2$, and the like) of the same probe. Finally, let $T_1$, $T_2$, and the like, denote sequences in the target polynucleotide that are not complementary to probe sequences (and do not hybridize therewith to any substantial extent). In this notation then, the target polynucleotide 50 would be written as $T_1$-$\overline{S}_1$-$T_2$-$\overline{S}_2$-$T_3$, while first and second probes of a target probe set would be written as:

$\overline{X}$-I-$S_1$ and $\overline{X}$-I-$S_2$.

Figure 5:
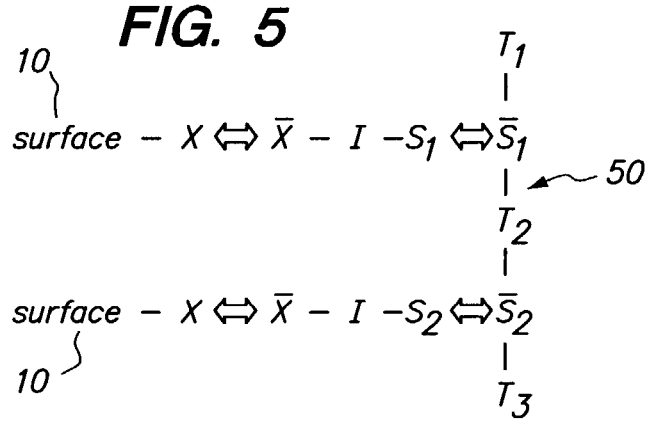
FIG. 5 illustrates an array and method of the present invention wherein target probes are indirectly linked to a substrate.

Kits of the present invention which use indirect binding of a target probe to the substrate then, would include an addressable array with a substrate 10 (designated as a "surface") in FIG. 5 having a predetermined feature at which are linked to substrate 10 capture probes X, as illustrated in FIG. 5. Other features (not shown in FIG. 5) on the array which may be intended for evaluating the presence of other target polynucleotides, may use respective other capture probes and/or target probes as described herein. The kit further includes a set of target probes $\overline{X}$-I-$S_1$ and $\overline{X}$-I-$S_2$, and possibly other different sets of target probes for other array features intended for other target polynucleotides. While it is preferable that the anti-target regions are of different sequence, they could possibly be the same (for example, both could be $S_1$) where a target polynucleotide has two spaced apart target regions of the same sequence. Also, while it is simplest and therefore preferable that the capture regions X at the predetermined feature are all the same, it is possible to use capture probes at the predetermined feature which have different sequence capture regions (such as $X_1$ and $X_2$) in which case different anti-capture sequences may be used (such as $\overline{X}_1$ and $\overline{X}_2$).

The use of a foregoing type of kit is also illustrated in FIG. 5. In FIG. 5, anti-target—target sequence duplex (hybrid) formation be denoted by ⇔. When a sample containing a target 50 is exposed to an array and target probes of the foregoing kit, under hybridizing conditions, the hybridization complex illustrated in FIG. 5 will form. That is, each of multiple molecules of target polynucleotide 50 will indirectly bind to the predetermined feature of the array to which is linked capture probes X. This occurs by anti-target regions $S_1$ and $S_2$ of the multiple target probes $\overline{X}$-I-$S_1$ and $\overline{X}$-I-$S_2$ forming simultaneous hybrids with target regions $\overline{S}_1$ and $\overline{S}_2$, respectively, and by the anti-capture regions $\overline{X}$ hybridizing with the capture regions of the capture probes X. This results in bidentate binding (that is, two points of attachment) of the target, via the target probes. The foregoing complex of this sort can be assembled in multiple steps, by hybridizing an array with a feature having linked capture probe X, to the set of target probes and then to target. In this case, the first-layer (bridging probes hybridized to the array) can be stabilized by UV photo-crosslinking or chemical crosslinking. Alternatively, the hybridization complex can be assembled by mixing the target and target probes together, then hybridizing the mixture to the array (either after the foregoing target/target probe mixing, or simultaneously with that mixing).

A kit of the present invention may carry an array on substrate 10, which has at least one feature as described in connection with FIG. 5. The kit further includes a container 300 with the set of target probes (typically mixed together) of FIG. 5. The mixture in container 300 may also include other sets of intermediate target probes, as well as reference polynucleotides (used, for example, to confirm hybridization conditions) or polynucleotide target probes in a preselected concentration but labeled differently from sample target probes of the same sequence target regions (used as references to determine relative amount of target sequence in a sample). All of the foregoing can be placed in a single package 410 along with instructions printed on a medium 400 (for example, paper). Alternatively, for kits with arrays in which the target probes are directly linked to substrate 10 as in FIGS. 3 and 4, the target probes need not be present in container 300 and further, if other types of mentioned probes are not required, container 300 can be dispensed with altogether.

Figure 6:
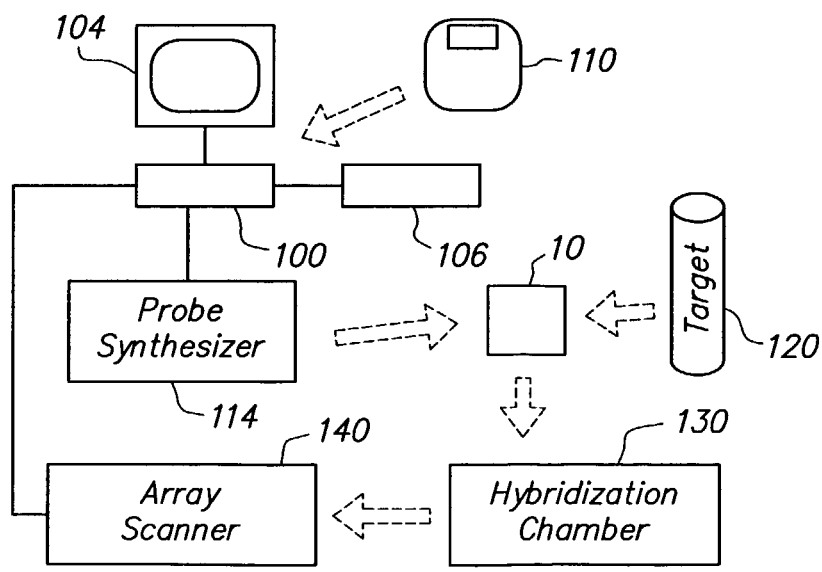
FIG. 6 is a schematic of an apparatus of the present invention and the use of such an apparatus in a probe evaluation method of the present invention.

Finding a set of suitable target probes (whether directly or indirectly bound to a substrate) can be an time consuming, since for any given target polynucleotide there can be a large number of potential sequences which can individually bind with all possible subsequences of a target polynucleotide. To then try all combinations of such possible potential sequences (for example, all possible combinations of two such sequences in the case where the target probe set has two members) becomes an unduly burdensome task. However, as mentioned above, the present invention provides an apparatus, and a method which can be executed by such an apparatus, for choosing good polynucleotide target probes for a target probe set of any of the types described above. One such apparatus is illustrated in FIG. 6, and includes a computer 100 having an operator display 104 and operator input device 106 (for example, a keyboard and/or mouse or other user operable pointing device). Computer 100 includes a programmable processor as well as a drive for loading an evaluation program from a computer program product in the form of a computer readable portable medium 110 (which may, for example, be a magnetic or optical disk or tape). The computer readable storage medium may comprise, for example: magnetic storage media such as magnetic disc (such as a floppy disc) or magnetic tape; optical storage media such as optical disc, optical tape, or machine readable bar code; solid state electronic storage devices such as random access memory (RAM), or read only memory (ROM); or any other physical device or medium which might be employed to store a computer program. It will be also be understood that computer 100 can be any hardware and/or software combination equivalent, which can execute the steps required by an evaluation method of the present invention.

Computer 100 is optionally connected to control an automated oligonucleotide probe synthesizer, which can either be of a type which creates probes of required sequences directly on a substrate 10, or can be a presynthesizer which synthesizes whole oligonucleotide probes for subsequent manually controlled or automated linking to substrate 10. A hybridization chamber 130 is capable of holding an array on substrate 10 and a fluid containing target polynucleotide provided from container 120, in contact under hybridizing conditions. An array scanner 140 is capable of observing the binding pattern of such an array and optionally directly relaying the results to computer 100. Alternatively, probe synthesizer 114 may be controlled by a user based on sequences output by computer 100 such as on display 104 or on a printer (not shown), and the observed binding pattern data generated by array scanner 140 may be input to computer 100 by a user (such as through input device 106).

It will be appreciated that in FIG. 6, any one or more of the illustrated components can be remote from the others, and any indicated connection can be performed through suitable communication channels for remote components (for example, through a suitable network, such as a telephone network or the internet).

Figure 7:
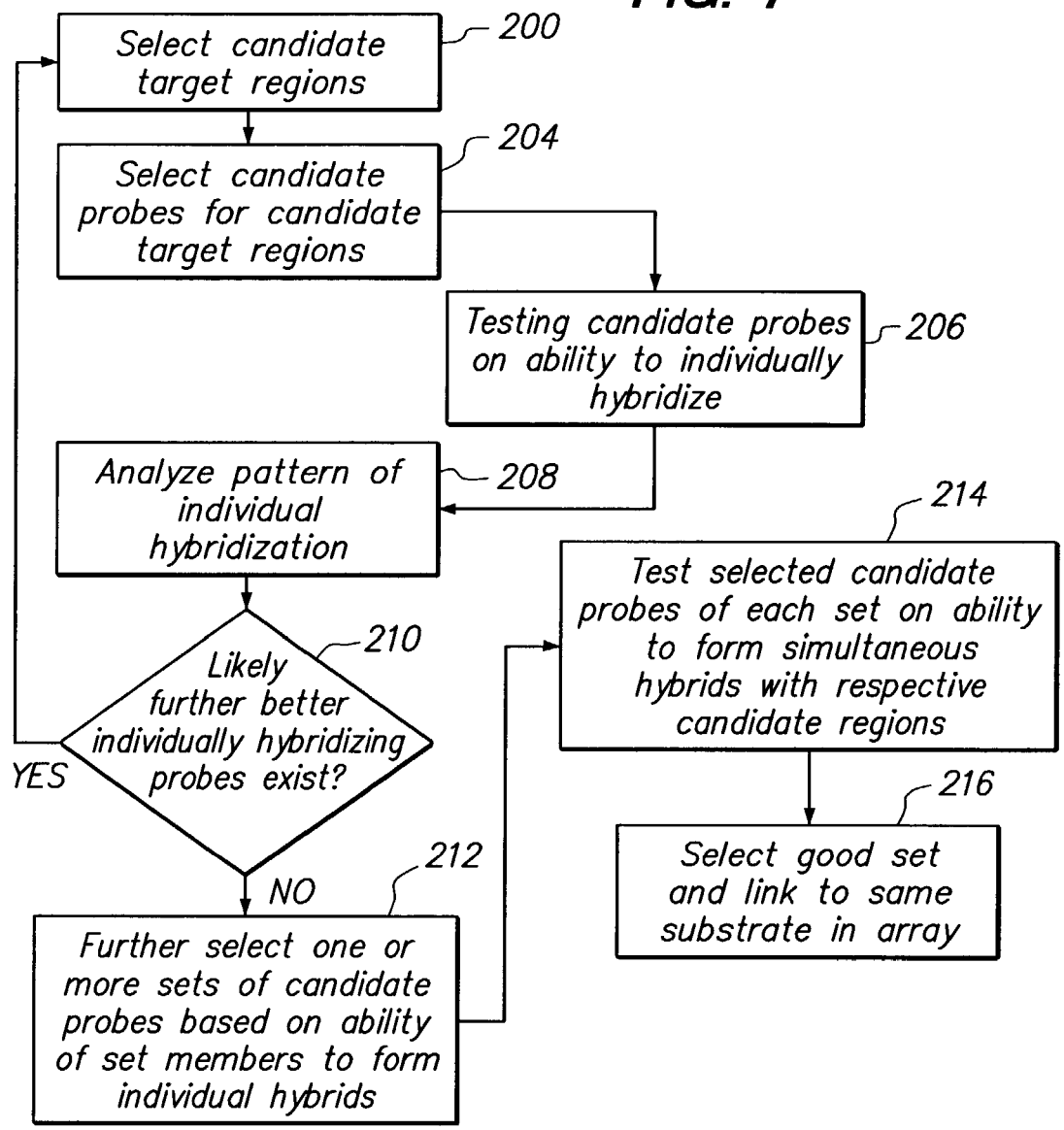
FIG. 7 is a flowchart illustrating a method of the present invention, including the steps executed by a computer program carried by a computer program medium of the present invention.
Figure 8:
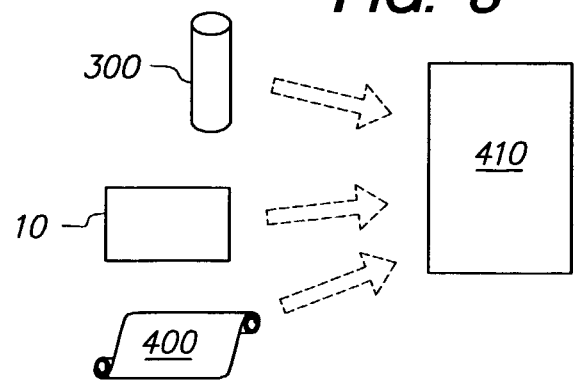
FIG. 8 illustrates a kit of the present invention.

Computer 100 is programmed by the program on medium 110, to execute some of the steps of a method of the present invention illustrated in FIG. 7. However, it will be appreciated that some or all of the following steps could be carried out manually by an individual. First, candidate target regions are selected (200). This selection can be based on any predetermined criteria. For example, candidate regions each of m nucleotides in length and spaced apart by n nucleotides along the target polynucleotide can be selected. Such criteria could also, for example, include access to a database of known good target regions for a particular polynucleotide. Candidate probes which can potentially hybridize with the selected respective candidate target regions are then selected (204). Typically the candidate probes are selected to have sequences which are exact complements of respective target regions. Each of the candidate probes are then tested (206) on their ability to individually hybridize with a corresponding target region. This testing step includes synthesizing the candidate probes at probe synthesizer 114 and linking them to a substrate 10 (if the candidate probes are not already linked to substrate 10 by virtue of being synthesized by in situ synthesis). Note that the candidate probes can be arranged in the form of one or more arrays on substrate 10, each array taking the form described in connection with FIGS. 1 to 3, except each array feature will typically bear only one candidate sequence. The testing (206) further includes exposing the resulting array to mixtures of target polynucleotides from container 120 and maintaining hybridization conditions while the two are in contact, by means of hybridization chamber 130. As part of the testing, the array is then removed from chamber 130 and the resulting binding pattern observed by scanning with array scanner 140, with the resulting data being received into computer 100.

The data, representing a pattern of individual hybridization of the candidate probes, is then analyzed (208) by computer 100. This analysis can be based on any suitable algorithm, for example where candidate regions each of m nucleotides in length and spaced apart by n nucleotides along the target polynucleotide were initially selected, the results for ability of such candidate regions to form individual hybrids versus the position of the target sequence along a target polynucleotide, can be analyzed as disclosed in more detail below. Based on the analysis, an evaluation can be made (210) as to whether better individually hybridizing probes might exist. For example, where the analysis is based on the foregoing ability versus target sequence position, if peaks exist in a plot of the data then it may be concluded that there may be at least one additional candidate target region (at least partially overlapping the n gap) which might allow for a better individually hybridizing probe. Such an additional candidate target region is selected and the foregoing steps of selecting a candidate target probe, and testing the so-selected candidate target probe, are repeated using that additional candidate target region. Further iterations of the same cycle can be repeated until it is concluded that it is unlikely that better individually hybridizing probes exist.

At this point, at least one set of at least two of the candidate probes which actually hybridized individually with at least a predetermined efficiency ("successful individually hybridizing candidate probes") with respective candidate regions of the same target polynucleotide, is then selected (212). The one set may include at least two, three or more candidate probes depending on what efficiency of multidentate binding of the target polynucleotide is desired (for example, bidentate, tridentate and the like). Further, multiple sets of such candidate probes may be selected depending upon the results of the individually hybridizing tests. Note that the "predetermined efficiency" can, for example, be some preselected lower limit, or alternatively a preselected number of the strongest hybridizing successful individually hybridizing candidate probes. This selection can, for example, simply be all possible combinations of two or more (depending on the efficiency of multidentate binding desired) successful individually hybridizing candidate probes. Each of the sets is then tested (214) on the ability of the candidate probes in the set, to form simultaneous hybrids with the respective candidate target regions. This testing includes fabricating and testing an array in a similar manner as described above in connection with FIG. 6 for testing the ability of candidate probes to individually hybridize to a respective candidate target regions. However, in the case of testing for ability of sets to form simultaneous hybrids, each feature 16 of the array will carry a mixture of the multiple different target probes of the set. In this regard, a portion of such a screening array may look and operate in essentially the same manner as described in connection with FIGS. 3 and 4.

One or more sets of candidate probes which actually formed simultaneous hybrids with respective candidate target regions with at least a predetermined efficiency, may then be selected as a "successful simultaneously hybridizing probe set". Again, the predetermined efficiency criterion can be any of those criteria mentioned above. One or more of such sets can be linked to a substrate 10 at respective features 16, to form at least part of an array of the present invention. Alternatively, where target probes are intended to be indirectly bound to the substrate through a capture probe, a suitable anti-capture sequence can be selected for the members of a target probe set based on the capture probe sequence.

EXAMPLE

A specific example of the process of selecting a simultaneously hybridizing probe set, will now be described.

Selection of Successful Individually Hybridizing Candidate Probes

Highly sensitive probe sequences specific to the cab, cor47 and sig1 genes of *Arabidopsis thaliana* and a portion of the pbpC gene of *E. coli* were determined by two-step iterative refinement. In the first step, every 10th possible 25-mer probe to each target was synthesized on an oligonucleotide array. Arrays were hybridized to rhodamine-6-G-labeled complementary RNA (cRNA) derived from each target. Labeled cRNA was produced by transcribing a template that placed a T7 RNA polymerase promoter at the 3' end of a given gene; rhodamine-6-G (R6G) was introduced by adding R6G-CTP (New England Nuclear, Boston, Mass.) to the nucleotide triphosphate mixture.

Hybridizations were performed overnight, at 37° C., in a solution containing 6×SSPE (900 mM sodium chloride/60 mM sodium phosphate/6 mM EDTA, pH 7.5), 0.05% w/v Triton X-100 (Amresco reagent grade, product code 0694), 100 µg/ml heat-denatured salmon sperm DNA, 1 mg/ml bovine serum albumin, 0.1% w/v sodium dodecyl sulfate and 200 pM cRNA. Arrays were washed with 0.1×SSPE (1:60 dilution of 6×SSPE) containing 0.005% Triton X-100, at 37° C., for 15 minutes. Washed arrays were dried and read using a confocal laser scanner.

Figure 9:
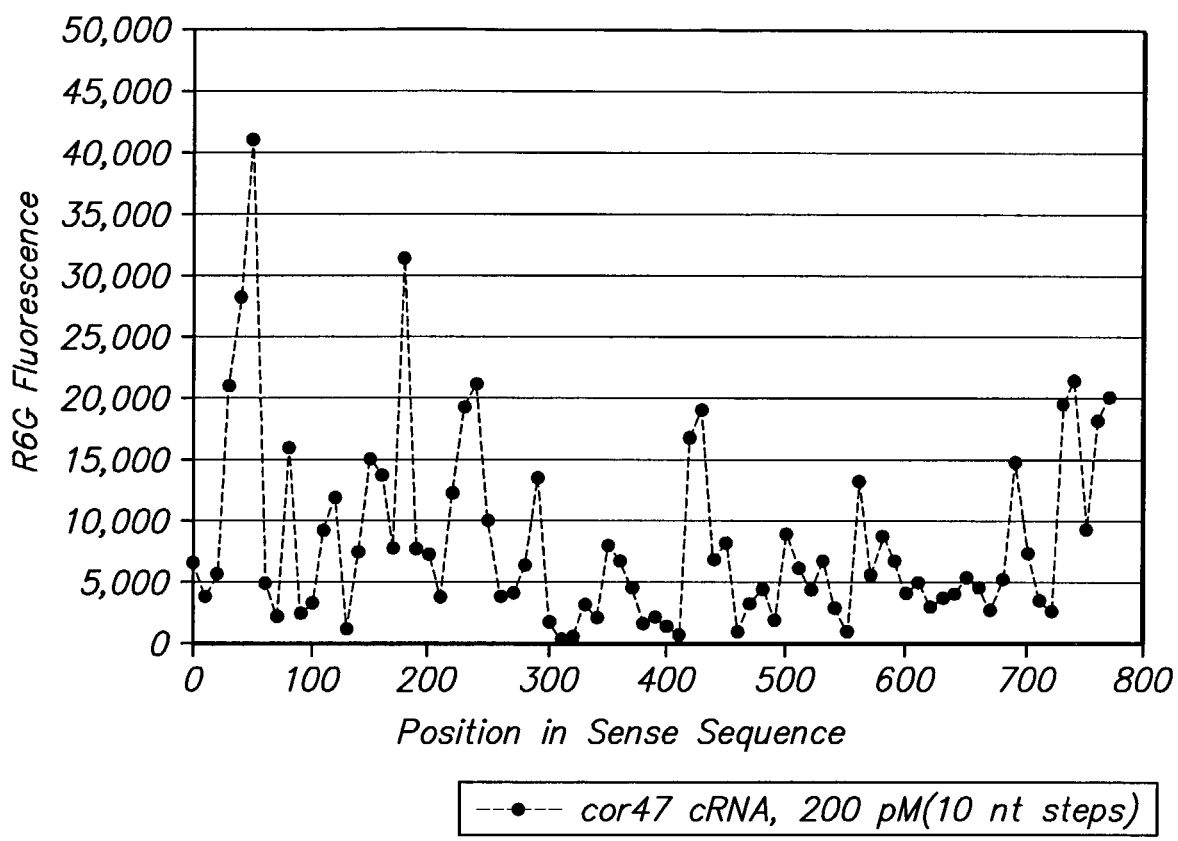
FIG. 9 is a graph illustrating experimentally determined binding efficiency of candidate probes to a target region, versus position of the target region along a target polynucleotide, as discussed further in the Example below.

The survey disks yielded "spectra" of probe efficiency: when plotted as a function of probe position in the target coding sequence, the hybridization signals formed a pattern of peaks and valleys. An example of such a spectrum for the cor47 gene is shown in FIG. 9.

The peaks observed in each hybridization spectrum were refined by a second experiment in which every other possible 25-mer probe in each hybridization peak was synthesized on an oligonucleotide array. Arrays were hybridized and read as described for the first peak refinement iteration. The results of the first and second design iteration were combined to pick between 6 and 10 optimized probes to each target; the probes discovered by this process are listed in Table 1 below.

It should be noted that such empirical probe discovery can be greatly aided by the use of probe design algorithms. Such algorithms generally use predicted thermodynamic properties of candidate probes to a given target to predict the approximate locations of peaks of hybridization efficiency. One such algorithm for selecting individually hybridizing probes, is disclosed in U.S. patent application Ser. No. 09/021,701, entitled "Methods for Evaluating Oligonucleotide Probe Sequences" filed Feb. 10, 1998 by Karen W. Shannon et al. and owned by the same assignee as the present application.

TABLE 1

| Gene | Probe Sequence | Probe Name | Seq. ID No. |
|------|---------------|------------|-------------|
| cor47 | GTACCAGTTTCCACTACCATCCCGG | cor47-25-0429 | 001 |
| cor47 | GAGGATTCACCAGCTGTCACGTCCA | cor47-25-0561 | 002 |
| cor47 | AGAGGTTACGGATCGTGGATTGTTT | cor47-25-0035 | 003 |
| cor47 | AGGAGAACAAGATTACTCTGCTAGA | cor47-25-0181 | 004 |
| cor47 | TGAGGAGAACAAGCCTAGTGTCATC | cor47-25-0233 | 005 |
| cor47 | AGAGTCTGATGATTAAGCAAAATGG | cor47-25-0737 | 006 |
| sig1 | TGGTTATGTCTATTGCTCAGCGTTA | sig1-25-0477 | 007 |
| sig1 | AGGGTGGTCTTATCGGACTTTTGCG | sig1-25-0537 | 008 |
| sig1 | GTCTTATCGGACTTTTGCGGGGAAT | sig1-25-0543 | 009 |
| sig1 | GGCTATGAGTAATGTGCGTTTGGTT | sig1-25-0457 | 010 |
| sig1 | GTGCTTAGTCATGTGGAAGTTGTGC | sig1-25-0263 | 011 |
| sig1 | GGTCTTCGTCTTGATGATCATAAGT | sig1-25-0311 | 012 |
| sig1 | GGATTCGACAGGGTGTCTCAAGAGC | sig1-25-0621 | 013 |
| sig1 | TACATTGCGGATACTCGTTTGGAGA | sig1-25-0893 | 014 |
| cab | CACTTGGCGGATCCATGGCACAACA | cab-25-0689 | 015 |
| cab | GGATTCTGTGTGCAACAGTCGGCTT | cab-25-0629 | 016 |
| cab | GCGCTGTTGGCGTTTGTAGGATTCT | cab-25-0611 | 017 |
| cab | GGAGAACTTGGCAACTCACTTGGCG | cab-25-0673 | 018 |
| cab | GTGTACCTTATGAGCTTTATGTGTA | cab-25-0767 | 019 |
| cab | AACATTGGCGATATTGTTATCCCTT | cab-25-0713 | 020 |
| cab | GCTCACTGGATGCCTGGCGAGCCAC | cab-25-0155 | 021 |
| cab | CATTGCATTTGTTGAGCACCAGAGA | cab-25-0463 | 022 |
| cab | GGTTTGACCCACTTGGACTTGGAGA | cab-25-0219 | 023 |
| cab | GTTCCTGGGATTTTGGTACCAGAAG | cab-25-0311 | 024 |
| pbpC | GCAGGTTGCTCGTCTGCTTGATCCT | pbp1-25-0233 | 025 |
| pbpC | CTCACTATGCAGGTTGCTCGTCTGC | pbp1-25-0225 | 026 |
| pbpC | GGTTATTTCCGGTGGCAGCACGCTC | pbp1-25-0203 | 027 |
| pbpC | TGCTTGATCCTCACCCCAAAACATT | pbp1-25-0247 | 028 |
| pbpC | CTCACTTCGGGACGGGTTATTTCCG | pbp1-25-0189 | 029 |
| pbpC | GTGGTCCCGTGAGCAGGTAAAAGAG | pbp1-25-0563 | 030 |
| pbpC | ATGCGTGTTCGCGGCTGGGTGGGAT | pbp1-25-0801 | 031 |
| pbpC | GGCGGTACGTTGCAGGGGATCGGTG | pbp1-25-0369 | 032 |
| pbpC | GGATTGCCGTTATATTTGCCCAACG | pbp1-25-1131 | 033 |

Selection of Successful Simultaneously Hybridizing Probe Set

Effective binary probe combinations (target probe sets) can then be determined by combinatorial means, using an array as the measurement device. First, test features are designed on the basis of the optimal probes previously determined for that target. For example, for the target cor47 (see Table 1), the binary probe combinations to be screened are (in terms of Sequence ID Numbers) 001&002, 001&003, 001&004, 001&005, 001&006, 002&003, 002&004, 002&005, 002&006, 003&004, 003&005, 003&006, 004&005, 004&006 and 005&006. This example is easily extended to the probe lists for each target considered in Table 1. In general, if probe optimization has defined N effective probes against a given target, then the number of binary probe combinations B to be screened is given by $$B = \frac{N(N-1)}{2}.$$

Screening is performed on an array that compares the hybridization efficiencies of the binary features to the hybridization efficiencies of the N original optimized probes. If each feature is repeated M times, then F, the total number of features needed, is given by $$F = M(B+N)$$
$$= M\left[\frac{N(N-1)}{2} + N\right]$$
$$= \frac{MN(N+1)}{2}$$

For the example of cor47, if M=3 (a minimal value for an optimization experiment), then F is 63. It is easy to see that the number of required features per gene is significant even if the best probes are picked prior to initiating optimization of binary combinations. However, pre-picking the best probes is much more efficient than testing all probe combinations. For example, testing all possible binary combinations of every other probe against cor47 (i.e. the set required to guarantee that the optimal combinations are all examined) requires an N of 369 (i.e. every other probe, starting at 1 and ending at 737). If M=3, then F is 204,795. This is almost twice the number of features available on the highest density arrays made by current commercial means, and is inconveniently large.

The above discussion can be generalized to features that combine k probes. In the general case, K, the number of unique combinations of k probes that can be produced from a set of N unique probes, is given by $$K = \frac{N!}{k!(N-k)!}.$$

The total number of features F required to compare all unique mixtures of k probes to the original set of N probes is given by $$F = M\left[\frac{N!}{k!(N-k)!} + N\right].$$

Again, the example of cor47 is instructive. If 6 pre-optimized probes are used in unique combinations of 3 (k=3) and measurements are repeated 3 times (M=3), F is 78. If the probes are not pre-optimized (N=369), then F is 24,918,939. Clearly, the use of pre-optimized probes is much more efficient.

During the initial screen of combination probe features, equimolar mixtures of probes are used. Based on the results of the initial screen, the best combinations are chosen for further optimization by systematic variation of the mole fraction of each component probe.

Determination of Optimum Stoichiometry of Probe Set

It would initially appear that the probability of multidentate binding of a target by a target probe set would be a maximum when all member probes are present in equal numbers. However, several effects can change the optimal mixture to one in which probes are not equally represented. The probes may not mix ideally. Binding of target to one probe may create a radial or angular "shadow", rendering other probes inactive. Some probes are capable of binding to more than one region of some targets. For these reasons, the relative concentrations of target probes in a set used to construct a multiprobe feature, should be optimized empirically. This can be accomplished by, for example, using some version of grid search (that is, test different probe set mixtures containing different relative concentrations of the member target probes, in an organized fashion, then use the surface shape to find the optimum), or via a statistical experimental design, such as a factorial or Taguchi design. Note that tests of a probe set at multiple relevant concentrations will generally be done under the same set of conditions (for example, same concentration of components, and same time and temperature). Generally, a grid search will be more efficient for binary or trinary of target probe sets. Statistical experimental designs are more efficient for combinations of many probes. Both approaches can be applied under the guidance of commercially available software packages any of which could be run by computer 100. In this event, it will be appreciated that computer 100 can also select the various concentrations of a selection successful simultaneously hybridizing probe set for testing, and receive and analyze the test results to select particular relative concentrations to be linked to a substrate at a predetermined feature, during fabrication of an array of the present invention.

The disclosed invention then, can provide high sensitivity for a target by using array probe features that contain a mixture of particular target probes. Such array features combine the affinity of long probes and the specificity of shorter probes.

Various modifications to the embodiments of the invention described above are, of course, possible. Accordingly, the present invention is not limited to the particular embodiments described in detail above.

What is claimed is:

1. A method of evaluating polynucleotide target probes on their ability to form simultaneous hybrids with respective regions of a same target polynucleotide molecule, the method comprising: (a) selecting candidate probes which can potentially hybridize with selected respective candidate target regions of the target polynucleotide, based on the sequence of the selected candidate target regions; (b) testing candidate probes on their ability to actually hybridize individually with respective candidate target regions; (c) further selecting at least two of the candidate probes which actually hybridized individually with at least a predetermined efficiency with respective candidate target regions; and (d) testing the selected candidate probes on their ability to form simultaneous hybrids with the respective candidate target regions.

2. A method according to claim 1 wherein the selected respective candidate target regions are spaced apart along the target polynucleotide.

3. A method according to claim 2 additionally comprising, selecting at least one additional candidate target region based on the results of step (b), and repeating steps (a) and (b) for the additional candidate target region.

4. A method of evaluating polynucleotide target probes on their ability to form, when linked to a same substrate, simultaneous hybrids with respective regions of a same target polynucleotide molecule, the method comprising: (a) selecting candidate probes which can potentially hybridize with respective candidate target regions of the target polynucleotide, based on the sequence of the candidate target regions; (b) testing candidate probes on their ability to actually hybridize individually with respective candidate target regions; (c) further selecting at least two of the candidate probes which actually hybridized individually with at least a predetermined efficiency with respective candidate target regions; and (d) testing the further selected candidate probes when linked to the same substrate, on their ability to form simultaneous hybrids with the respective candidate target regions.

5. A method according to claim 4 additionally comprising repeating step (d) with modified relative concentrations of the further selected candidate probes.

6. A method according to claim 4 wherein in step (d), two selected candidate probes are tested on their ability to form simultaneous hybrids with respective candidate target regions.

7. A method according to claim 4 wherein the selected respective candidate target regions are spaced apart along the target polynucleotide.

8. A method according to claim 4 additionally comprising, following step (c), selecting at least one additional candidate target region based on the results of step (b), and repeating steps (a) and (b) for the additional candidate target regions.

9. A method according to claim 8 wherein the hybridization pattern comprises the hybridization efficiency.

10. A method according to claim 4 wherein the candidate probes are selected which are exact complements to respective candidate target regions.

11. A method according to claim 4 wherein the tested candidate probes in step (b) are linked to a substrate.

12. A method according to claim 11 wherein the tested candidate probes in step (b) are linked to a same substrate in the form of an addressable array.

13. A method of fabricating an addressable array of multiple polynucleotide probes linked to the substrate, comprising: (a) evaluating polynucleotide target probes according to the method of claim 1; and (b) linking the further selected candidate probes which actually formed simultaneous hybrids with the respective candidate target regions with at least a predetermined efficiency, to the substrate at a predetermined feature.

* * * * *